(12) United States Patent
Luksch et al.

(10) Patent No.: US 10,143,542 B1
(45) Date of Patent: Dec. 4, 2018

(54) DENTURE AND METHOD OF MANUFACTURING

(71) Applicant: O'Brien Dental Lab, Inc., Corvallis, OR (US)

(72) Inventors: Derrick G Luksch, South Beach, OR (US); Christophorus D. Luksch, Corvallis, OR (US)

(73) Assignee: O'BRIEN DENTAL LAB, INC., Corvallis, OR (US)

( * ) Notice: Subject to any disclaimer, the term of this patent is extended or adjusted under 35 U.S.C. 154(b) by 0 days.

(21) Appl. No.: 15/702,348

(22) Filed: Sep. 12, 2017

Related U.S. Application Data

(60) Provisional application No. 62/394,578, filed on Sep. 14, 2016.

(51) Int. Cl.
*A61C 13/20* (2006.01)
*A61C 13/10* (2006.01)
*A61C 13/01* (2006.01)

(52) U.S. Cl.
CPC .............. *A61C 13/20* (2013.01); *A61C 13/01* (2013.01); *A61C 13/1003* (2013.01)

(58) Field of Classification Search
CPC ...... A61C 13/01; A61C 13/20; A61C 13/1003
See application file for complete search history.

(56) References Cited

U.S. PATENT DOCUMENTS

| | | | |
|---|---|---|---|
| 3,727,309 | A | 4/1973 | Huey |
| 3,839,796 | A | 10/1974 | Hazar |
| 3,889,374 | A | 6/1975 | Saffir |
| 4,012,838 | A | 3/1977 | Abdenour |
| 4,094,067 | A | 6/1978 | Hazar |
| 4,971,735 | A | 11/1990 | Uebayashi |
| 5,294,380 | A | 3/1994 | Okamoto |
| 6,270,701 | B1 | 8/2001 | Kuroda |
| 6,534,562 | B2 | 3/2003 | Gen et al. |

*Primary Examiner* — James Sanders
(74) *Attorney, Agent, or Firm* — John Connors; Connors & Assoc. pc

(57) ABSTRACT

Our method applies a continuous pressure to an exterior of a denture setup during the polymerizing and shrinking of the plastic material forming a portion of our denture. The direction from which shrinkage occurs is controlled using a constant pressure of water. Application of at least 300 pounds per square inch (psi) of water pressure during polymerization continually forces a critical inside denture surface being formed against a master model surface to allow the major shrinkage to take place on a less critical outside denture surface, thereby reducing distortion to the interior (fitted) portion of the denture. This pressure reduces the size of the air bubbles to maximize the density of the polymerized denture material, thereby lowering oral fluid sorption into our denture. Thus our denture overall is a stronger, better fitting, durable product that addresses the esthetic, health and hygiene issues presented by conventional dentures.

3 Claims, 13 Drawing Sheets

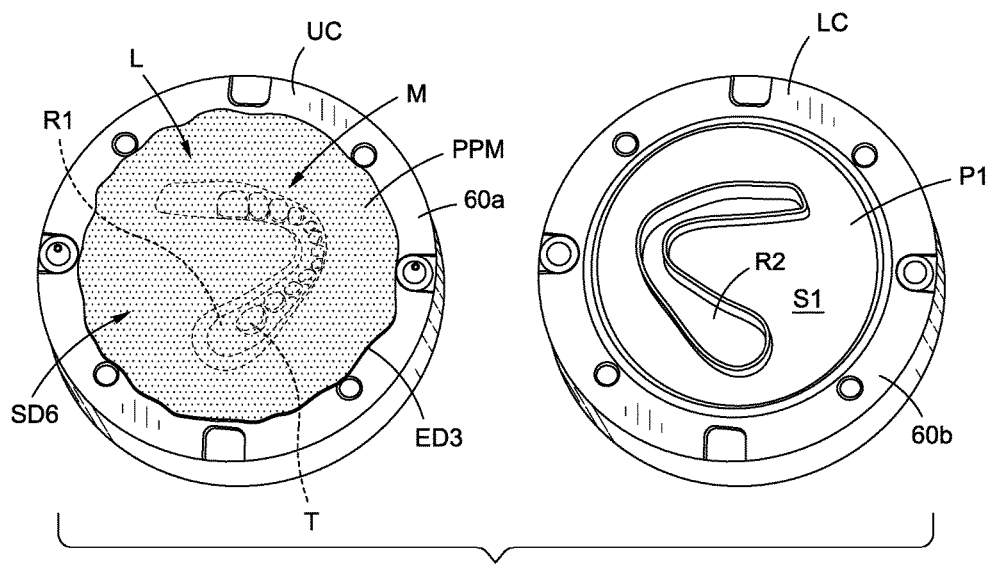
Fig. 7B
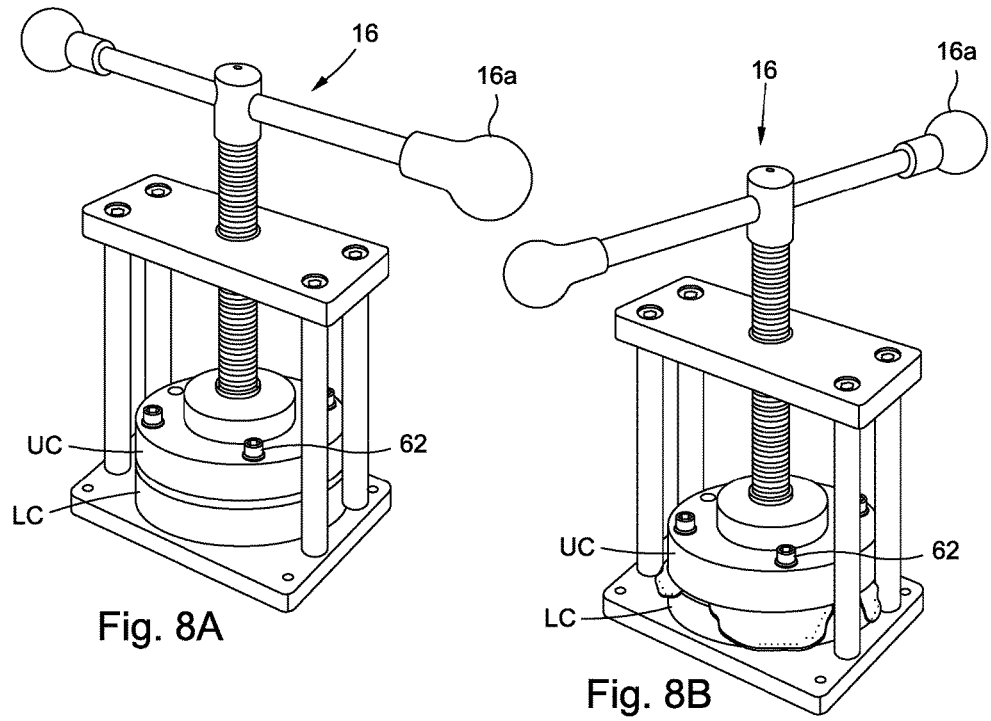
Fig. 8A
Fig. 8B

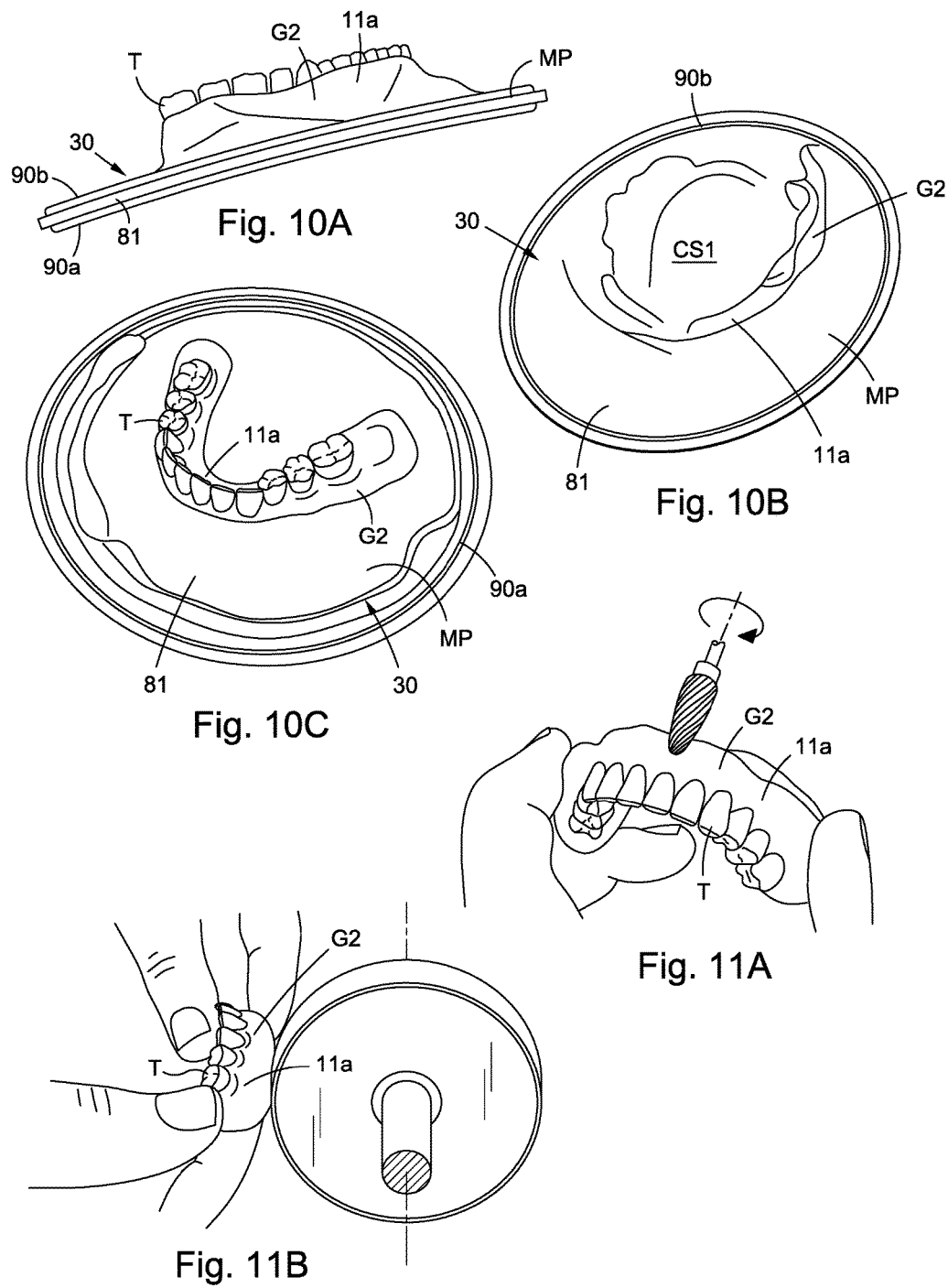

DENTURE AND METHOD OF MANUFACTURING

RELATED PATENT APPLICATIONS & INCORPORATION BY REFERENCE

This non-provisional utility patent application claims the benefit under 35 USC 119(e) of U.S. Provisional Patent Application No. 62/394,578, entitled "Denture And Method Of Manufacturing" filed Sep. 14, 2016. This related application is incorporated herein by reference and made a part of this application. If any conflict arises between the disclosure of the invention in this non-provisional application and that in the related provisional application, the disclosure in this non-provisional application shall govern. Moreover, any and all U. S. patents, U. S. patent applications, and other documents, hard copy or electronic, cited or referred to in this application are incorporated herein by reference and made a part of this application.

DEFINITIONS

The words "comprising," "having," "containing," "holding," and "including," and other forms thereof, are intended to be equivalent in meaning and be open ended in that an item or items following any one of these words is not meant to be an exhaustive listing of such item or items, or meant to be limited to only the listed item or items.

The word "plaster" includes dental stone and equivalent materials used in making denture molds.

BACKGROUND

Dentures have been on the market since the 1930's, using pretty much the same basic materials. While various attempts have been made to improve the process and provide for a better end result, until now no one has come close to achieving what we have accomplished using our method of manufacturing. The standard acrylic material used to simulate a patient's gum and hold in position artificial teeth embedded in the material is poly methyl methacrylate (PMMA). This acrylic material has two major inherent shortcomings associated with the current processing and polymerization of the material.

The primary issue is shrinking of material during the curing process. This results in less than a perfect adaptation and fit to a master model of the patient's internal mouth surfaces. Conventional processing systems used today require the acrylic material to polymerize under a static pressure in a two-part plaster mold having a cavity with dimensions corresponding to an exact fit for the patient. A polymerizable acrylic material is loaded into this cavity, and when the acrylic material begins to polymerize it shrinks into itself from all sides and in all dimensions. This distorts the finished denture, resulting in a denture that is smaller than the cavity that corresponds to the exact denture fit for the patient. Therefore conventional processes for manufacturing a denture do not result in the best denture fit possible.

The secondary issue is that all existing acrylic materials produce an end product that has varying degrees of microporosity, or air bubbles. Porosity allows for infiltration of oral fluids, leading to dis-colorization of the denture and bacterial growth that can result in hygiene and health issues. In addition, an increase in porosity directly decreases the strength and durability of the acrylic material and therefore the end denture product.

This background discussion is not intended to be an admission of prior art.

SUMMARY

Our method of manufacturing a customized denture for an individual patient has one or more of the features depicted in the embodiments discussed in the section entitled "DETAILED DESCRIPTION OF SOME ILLUSTRATIVE EMBODIMENTS." The claims that follow define our method and the denture made therefrom using a material that shrinks during the manufacturing. Our method forms a bearing surface of the manufactured denture that has a topography complementary to an interior surface of the patient's mouth that contacts the manufactured denture. Without limiting the scope of our method and denture as expressed by these claims, in general terms, some, but not necessarily all, of their features are:

One, our method of manufacturing produces a denser denture product that lowers oral fluid sorption. During polymerization, the application of a high water pressure generally from 300 to 600 psi is employed. Even at the lower pressure of 300 psi (approximately equal to 20 bar atmospheres of pressure), this pressure reduces the size of air bubbles in the polymerized acrylic material forming the artificial gum to $\frac{1}{20}$ of what is currently found using conventional processing methods. Thus, porosity in the gum of our denture is almost eliminated.

Two, our denture conforms to a patient's internal mouth surfaces that are critical to achieving a near perfect fit. As conventional, our denture comprises an array of artificial teeth projecting outward from a teeth support structure comprising an artificial gum. The teeth support structure has a bearing surface that mates with the patient's internal mouth surfaces. The artificial gum is formed from a membrane of poly methyl methacrylate and is polymerized under the high water pressure. The central feature of our denture is that during polymerization the membrane is subjected to an elevated water pressure in excess of 300 psi that continually forces the membrane against a mold surface corresponding to the patient's internal mouth surfaces to allow major shrinkage to take place on a less critical outside denture surface. This reduces distortion of the bearing surface and the size of any air bubbles in the poly methyl methacrylate so the density of the polymerized poly methyl methacrylate is at a maximum.

Three, in one embodiment, our method includes the steps of (a) preparing a denture setup that is a model of the denture being manufactured, the denture setup comprising a base having an interface surface portion having a topography that corresponds to the interior surface of the patient's mouth that bears against the manufactured denture, an external surface portion opposite the interface surface portion, an array of artificial teeth corresponding to the patient's teeth positioned upright in the interface surface portion and extending outward from the interface surface portion to correctly match opposed patient's teeth during biting, and a wax applied to the array of teeth and formed into a naturally appearing gum corresponding to the patient's gum, (b) providing a two-component container having a first component and a second component, the components configured to be assembled into a unitary container structure and having open mouths with matching shaped perimeters and facing each other in registration upon assembly, the components having complementary shaped perimeters of the mouths of the components that engage upon assembling said components to provide a seal, the assembled components being adapted to receive water under pressure that is applied to the denture setup positioned within the assembled container, (c) with the components disassembled, filling the first component with an unhardened plaster to form a first part of a two-part plaster mold for the denture setup, the first part including a first surface that lies along a plane within the open mouth of the first component, (d) positioning the denture setup on the unhardened first surface of the unhardened plaster and pressing the denture setup down into the unhardened plaster to generally position the interface interior surface portion in the plane of the unhardened first plaster surface lying with the open mouth denture.

(e) forming on the hardened first surface a wax gasket that has a first side that covers the first surface and the base of the denture set up to surround the wax material forming said naturally appearing gum corresponding to the patient's gum, the wax gasket having a perimeter that extends beyond the perimeter of the open mouth of the first component and an inner edge that abuts the wax material to form a margin along the wax material corresponding to a patient's gum line, (f) assembling the first and second components with the wax gasket between the components, filling the second component with an unhardened plaster, and allowing the plaster in the second component to set and harden to form a second part of the two-part plaster mold for the denture setup, the second part including a second surface that is within the open mouth of the second component upon filling the upper component with the unhardened plaster, the second surface contacting a second side of the wax gasket upon assembly of the components, (g) disassembling the components of the container and removing the wax gasket and wax material forming said naturally appearing gum corresponding to the patient's gum to expose the hardened first and second surfaces of the parts of the two-part plaster mold, the second surface having a recess with the array of artificial teeth corresponding to the patient's teeth positioned therein and the first surface having a recess complementary to the recess containing the teeth, (h) applying to the second surface a layer of polymerizable plastic material to form a membrane that covers the recess with the artificial teeth therein and has a perimeter that extends beyond the perimeter of the open mouths of the first and second components, (i) again assembling the first and second components and compressing the membrane of polymerizable plastic material between the first and second surfaces in the assembled components of the container, (j) initiating polymerization of the plastic material, and during polymerization, introducing into the assembled container water at a high pressure above atmospheric pressure to push the plastic material into the recesses to fill them with plastic material and force the plastic material away from the second mold surface and against the first mold surface to form from the polymerized plastic material a gum corresponding to the patient's gum and a bearing surface of the denture that has a topography complementary to the interior surface of the patient's mouth bearing against said bearing surface, and (k) removing any excess polymerized plastic material formed around the artificial teeth and polymerized plastic material forming a gum corresponding to the patient's gum, thereby providing the customized denture for the individual patient.

In summary, our method applies a continuous pressure to an exterior of a denture setup during the polymerizing of the acrylic material and shrinking thereof. While our method cannot eliminate shrinkage entirely, we control the direction from which shrinkage occurs using a constant pressure of water. Application of at least 300 pounds per square inch (psi) of water pressure during polymerization continually forces an inside denture surface being formed against a mold surface to allow the major shrinkage to take place on the less critical outside denture surface. This reduces distortion of the interior surface portion of the denture that is to be fitted as closely as possible to the patient's inside mouth surface. In other words, the polymerizable plastic material is constantly pressed against a mold surface that corresponds in topographical features to the inside of the patient's mouth that contacts the denture. Thus, the best denture fit possible. Consequently, our method delivers an overall stronger, better fitting, more durable denture that addresses the esthetic, health and hygiene issues presented by today's dentures.

These features are not listed in any rank order nor is this list intended to be exhaustive.

DESCRIPTION OF THE DRAWING

Some embodiments of our denture and method of manufacturing are discussed in detail in connection with the accompanying drawing, which is for illustrative purposes only. This drawing includes the following figures (Figs.), with like numerals and letters indicating like parts:

FIG. 7B is perspective view of the disassembled container showing one mold part surface covered with the membrane of un-polymerized plastic material and the other mold part surface uncovered and bare.

FIG. 8A is perspective view of the assembled container in a press with the layer of layer of polymerizable plastic material between the upper and lower components of the container and the mold part surfaces shown in FIG. 7B being pressed together.

FIG. 8B is perspective view of the assembled container with the press actuated to press excess polymerizable plastic material from between the juxtaposed plaster mold surfaces prior to polymerizing the material.

FIG. 10A is a side view of an unfinished denture retained in a sheet of polymerized membrane material removed from the disassembled container.

FIG. 10B is perspective view of the unfinished denture depicted in FIG. 10A showing the contact surface of denture that bears against the patient's tissue.

FIG. 10C is perspective view of the unfinished denture depicted in FIG. 10A showing the side denture opposed to the denture's contact surface.

FIG. 11A is perspective view of the sheet polymerized material retaining the unfinished denture shown in FIG. 10A cut away and being ground to remove excess, marginal polymerized material to finish the lower full denture.

FIG. 11B is perspective view of our finished lower full denture being polished to enhanced the appearance of our denture.

DETAILED DESCRIPTION OF SOME ILLUSTRATIVE EMBODIMENTS

General

Our denture conforms to a patient's internal mouth surfaces that are critical to achieving a near perfect fit in the patient's mouth. It comprises an array of artificial teeth projecting outward from a teeth support structure including an artificial gum. The teeth support structure is formed from poly methyl methacrylate under a pressure in excess of 300 psi that is directed to continually force an inside denture surface portion being formed against a mold surface. This allows major shrinkage to take place on a less critical outside denture surface. Consequently, distortion to the inside surface portion of the denture is reduced. Moreover, the size of any air bubbles are also reduced by a factor of greater than twenty so the density of the polymerized poly methyl methacrylate is maximized.

Figure 12A:
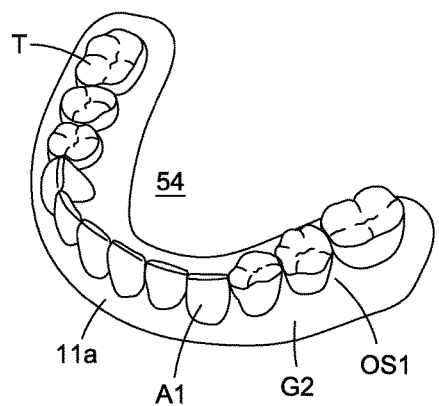
FIG. 12A is perspective view of our finished lower full denture showing the exterior of the denture.
Figure 12B:
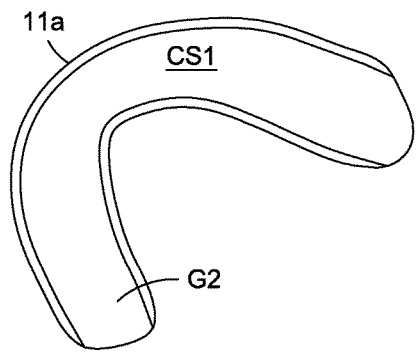
FIG. 12B is perspective view of our finished lower full denture showing the interior of the denture.
Figure 13A:
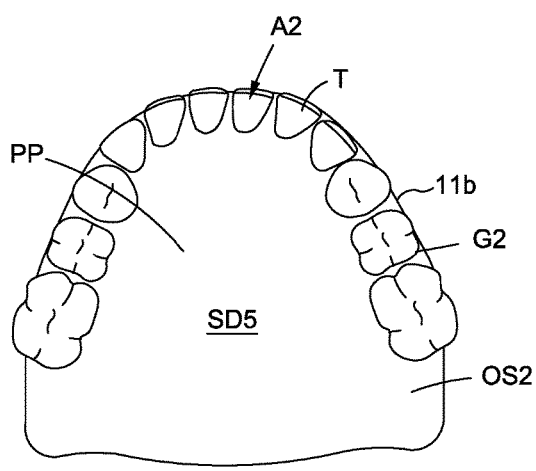
FIG. 13A is perspective view of our finished upper full denture showing the exterior of the denture.
Figure 13B:
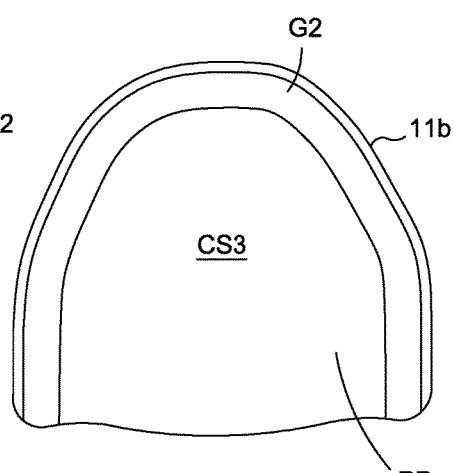
FIG. 13B is perspective view of our finished upper full denture showing the interior of the denture.

In our improved method of manufacturing a customized denture for an individual patient, during polymerization of a polymeric denture material, pressurized water above atmospheric pressure is introduced into a conventional denture setup to press a layer of the polymeric material against an interface mold surface portion of a denture setup. The interface surface portion has a topography that is complementary to an interior surface of the patient's mouth that bears against a contact surface of the denture formed from the polymerized polymeric material. Thus the contact surface on the denture mates closely with the interior surface of the patient's mouth. Our method may be used to make full or partial dentures of the upper teeth and the lower teeth. FIGS. 12A and 12B illustrate a full lower denture 11a, and FIGS. 13A and 13B illustrate a full upper denture 11b.

In the case of the full lower denture 11a shown in FIGS. 12A and 12B, an array A1 of teeth T is arranged in a generally U-shape and the denture's contact surface CS1 (FIG. 12B) has a topography that is complementary to the lower interior surface of the patient's mouth. In other words, the contact surface CS1 and lower interior surface of the patient's mouth fit snugly together with complementary surfaces abutting and essentially no space between them. In the case of the full upper denture 11b shown in FIGS. 13A and 13B, an array A2 of teeth T is arranged in a generally U-shape surrounding a palate portion PP and the denture's contact surface CS3 (FIG. 13B) has a topography that is complementary to the upper interior palate surface of the patient's mouth. In other words, the contact surface CS3 and upper interior surface of the patient's mouth fit snugly together with complementary surfaces abutting and essentially no space between them.

Method

Preparing a Denture Setup that is a Model of the Denture being Manufactured

Figure 2:
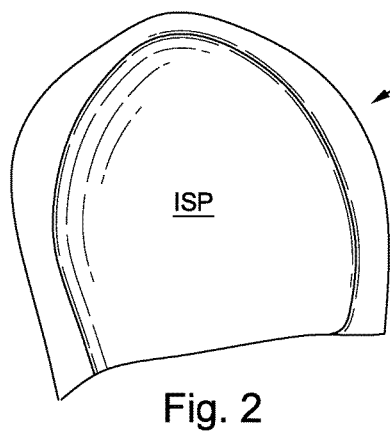
FIG. 2 is a perspective view of the plaster base of the denture setup shown in FIGS. 2A through 2C depicting an interface surface portion [ISP] with topographical features of the soft tissue surface of the patient's mouth that contacts the denture being manufactured.
Figure 2A:
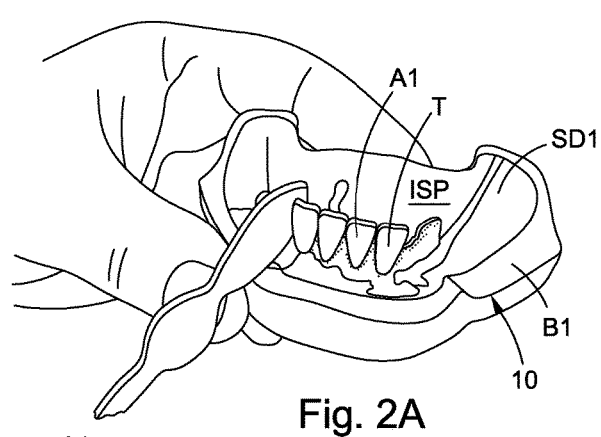
FIGS. 2A and 2B are perspective views of a denture setup for a lower full denture being prepared in accordance with conventional practice for a denture setup.
Figure 2B:
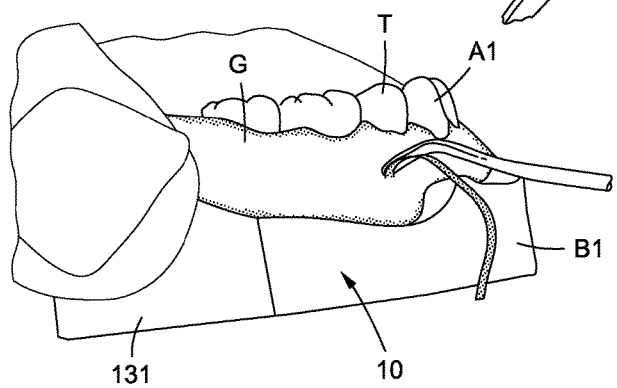
Figure 2C:
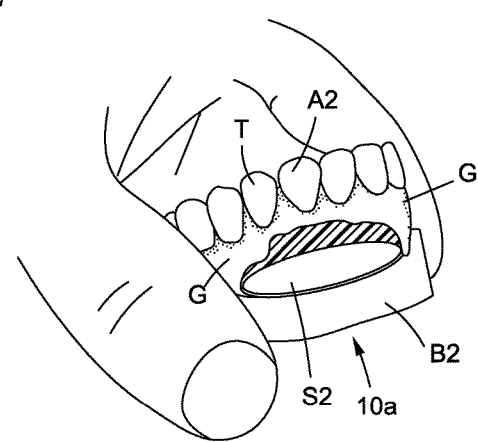
FIG. 2C is a perspective view, with sections broken away, of a lower full denture setup being prepared in accordance with conventional practice for denture setup.

Our method of manufacturing a customized denture for an individual patient uses conventional practices for preparing a denture setup; for example, as depicted in FIGS. 2A and 2B, a denture setup 10 for a lower full denture, or as depicted in FIG. 2C, an upper full denture setup 10a. Each denture setup 10 and 10a includes a plaster base B1 or B2, as the case may be, having a critical interface surface portion ISP (FIG. 2). The topographical features of the interface surface portion ISP are formed using an impression of the patient's mouth and correspond exactly to the soft tissue surface of the patient's mouth that contacts the denture manufactured using our method. Consequently, the topography of a contact surface of the finished denture that bears against the interface surface portion ISP is complementary to the interior surface of the patient's mouth. This internal contact surface CS1 of the finished lower denture 11a is shown in FIG. 12B, and this internal contact surface CS3 of the finished upper denture 11b is shown in FIG. 13B. Opposite these contact surfaces CS1 and CS3, respectively, is a non-critical external denture surface OS1 in the denture 11a and a non-critical external denture surface OS2 in the denture 11b.

As depicted in FIGS. 2A and 2B, a wax applied to an array of artificial teeth T is formed into a naturally appearing wax gum G corresponding to the patient's gum. The artificial teeth T correspond to the patient's teeth and are positioned upright in the wax gum G, with the root 70 (FIGS. 5 and 6B) of each tooth resting on the interface surface portion ISP and extending outward from the interface surface portion to correctly match opposed patient's teeth during biting. In the setup 10 (FIGS. 2A and 2B), there is the array A1 projecting outward from the one side SD1 of the base B1. In the setup 10a (FIG. 2C), there is the array A2 projecting outward from the one side S2 of the base B2. The wax is applied between and around the teeth T of the arrays A1 and A2 and formed into a naturally appearing wax gum G corresponding to the patient's gum.

Providing a Two-Component Container

FIGS. 1A through 1D, illustrate a metal two-component container 12 having a lower cylindrical component LC and an upper cylindrical component UC. Each component LC and UC has, respectively, a flange 60a and 60b forming an open mouth OM1 (FIG. 1D) and OM2 (FIG. 1C), respectively. Each component UC and LC has, respectively, a predetermined height h1 and height h2 that are equal. Each open mouth OM1 and OM2 has the same diameter, and each open mouth is configured to be assembled into a unitary structure with the open mouths facing each other and in registration with the flanges abutting. Bolts 62 (FIG. 5) fasten the flanges 60a and 60b together upon assembly of the upper component UC with the lower component LC. As discussed subsequently in greater detail, and depicted in FIG. 9B, the assembled container components UC and LC are adapted to receive water under pressure applied to a denture setup positioned within the assembled container 12.

Figure 1A:
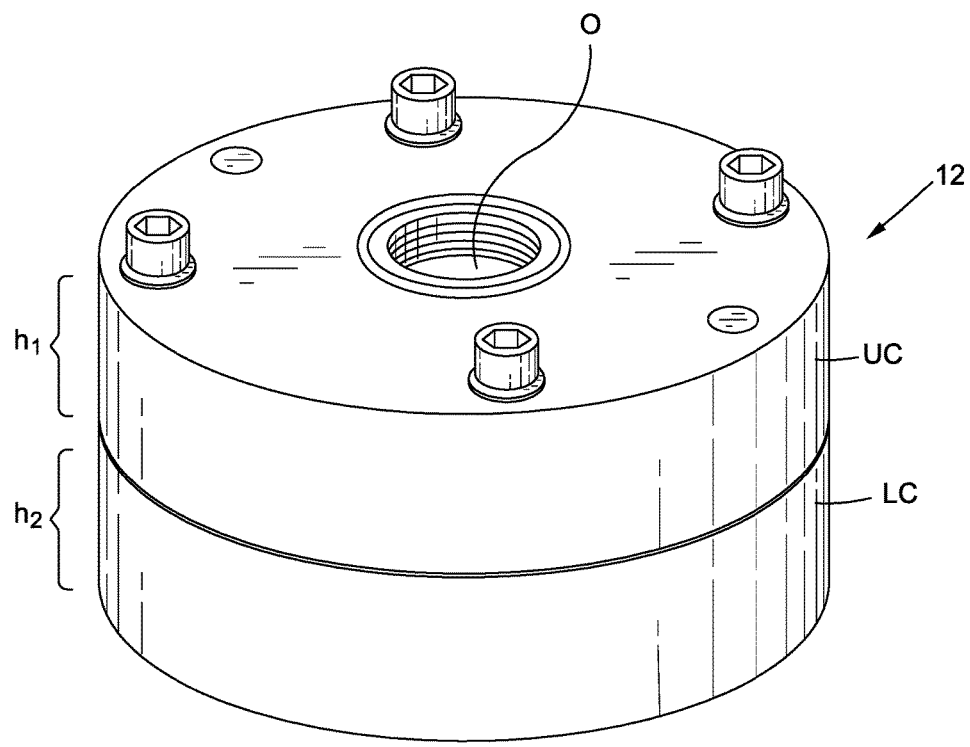
FIG. 1A is a perspective view of the assembled two-component container used in our method of manufacturing our denture.
Figure 1B:
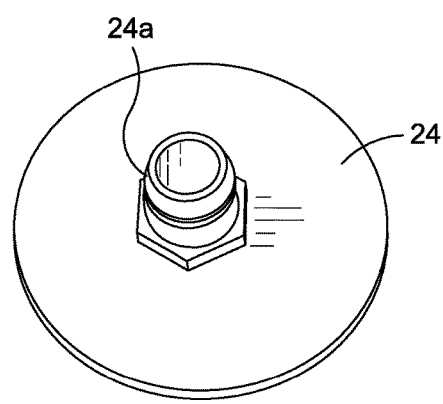
FIG. 1B is a perspective view of a central plug configured to be screwed into a central opening in an upper component of the two-component container shown in FIG. 1A.
Figure 1C:
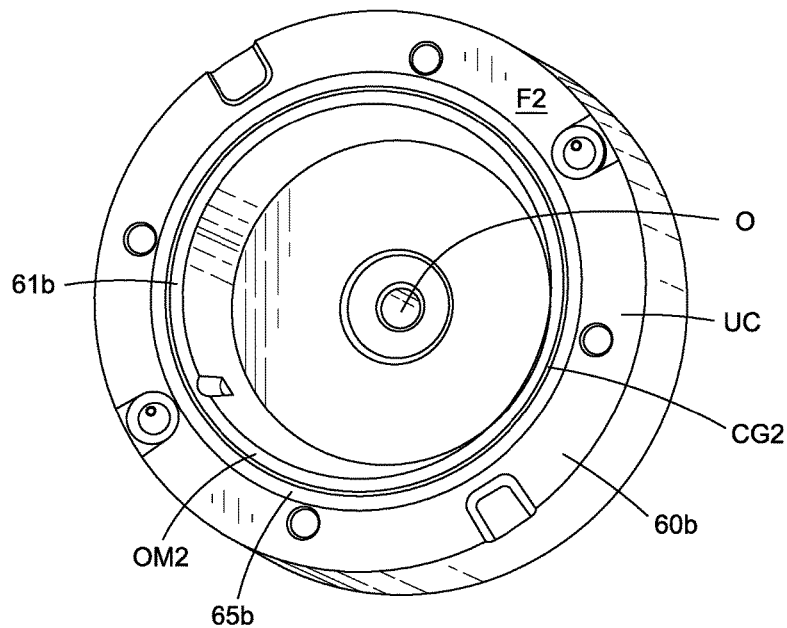
FIG. 1C is a perspective view looking into the interior of a upper component of the unassembled two-component container shown in FIG. 1A.
Figure 1D:
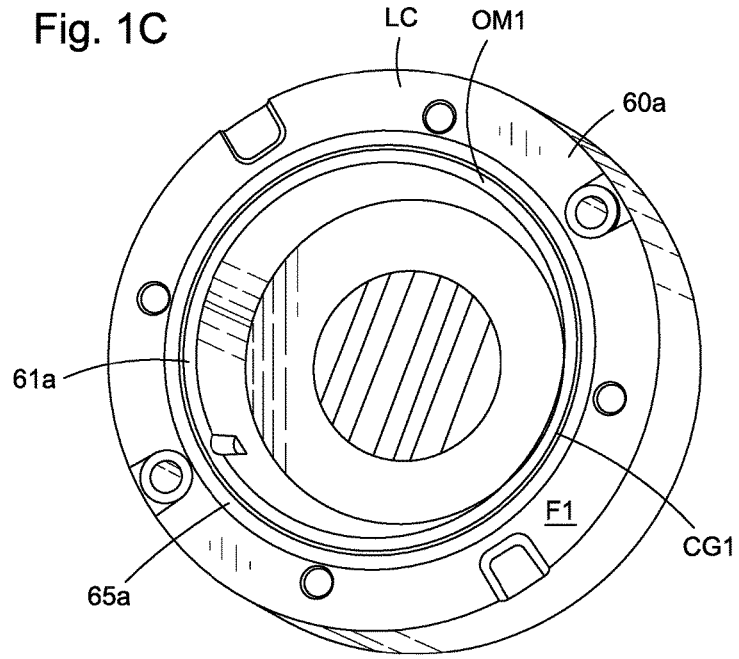
FIG. 1D is a perspective view looking into the interior of the lower component of the unassembled two-component container shown in FIG. 1A.

As best shown in FIGS. 1C, 1D, 5, and 5A, the flanges 60a and 60b and the open mouths OM1 and OM2 have complementary configurations that upon assembling the upper component UC and lower component LC they engage the wax gasket WG to provide a seal. This seal prevents unhardened plaster subsequently poured into the assembly of the components from seeping into the lower component LC. Specifically, as depicted in FIG. 1D, in a face F1 of the flange 60a is a circular groove CG1 between a circular land 61a and a circular step 65a at the mouth OM1. And as depicted in FIG. 1C, in a face F2 of the flange 60b is a circular groove CG2 between a circular land 61b and a circular step 65b at the mouth OM2. Upon assembly of the components, the circular grooves CG1 and CG2, as discussed subsequently in greater detail, in one step of our denture manufacturing method receive a wax gasket material and in another step of our method receive a polymerizable membrane material. During the different steps of our method, these materials are forced into the circular grooves CG1 and CG2 either manually, through water pressure, or using a press.

Forming a First Part of a Two-Part Plaster Mold for the Denture Setup

Figure 3A:
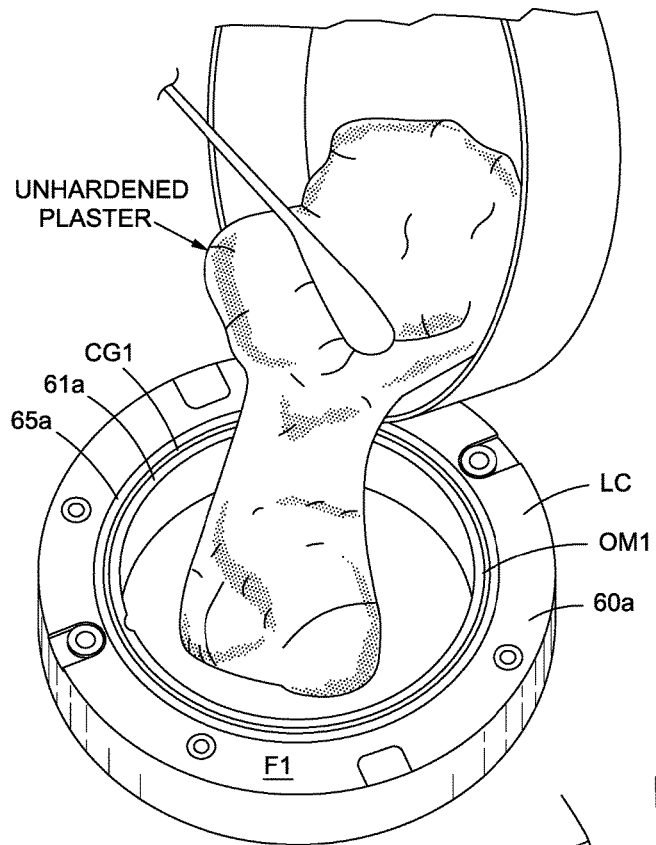
FIG. 3A is a perspective view of the lower component of the two-component container being filled with an unhardened plaster up to an open mouth of the lower component to form the lower part of a two-part plaster mold for the denture setup depicted in FIGS. 2A and 2B.

As shown in FIGS. 3A through 5A, a two-part plaster mold PM (FIG. 5) having a part P1 and a part P2 is formed within the container 12. Initially as illustrated in FIG. 3A with container components UC and LC disassembled, the lower component LC is filled with an unhardened plaster to form the lower part P1 of the two-part plaster mold PM. Upon filling the container lower component LC with unhardened plaster to the level of the open mouth OM1 as depicted in FIG. 3B, a first plaster mold surface S1 (FIG. 6C) within this open mouth is formed.

Positioning the Denture Setup on the Unhardened First Surface

Figure 3B:
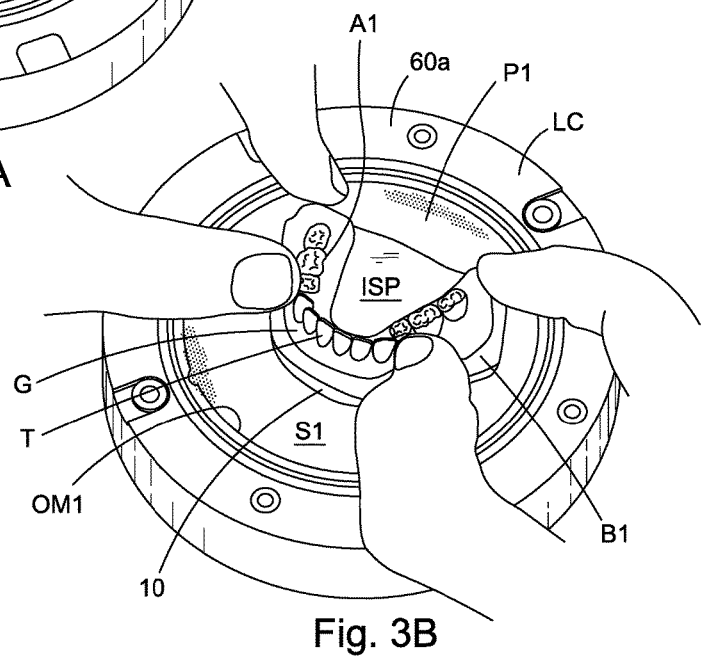
FIG. 3B is a perspective view the denture setup depicted in FIGS. 2A and 2B being positioned on an exposed surface of the unhardened plaster and pressed into this exposed surface locating the denture setup within the perimeter of an open mouth of the lower component of the two-component container.

As shown in FIG. 3B, the denture setup 10 or 10a, as the case may be, is located on the unhardened, first plaster mold surface 51. The denture setup 10 or 10a is manually oriented and the base B1 or B2, as the case may be, of the denture setup is pressed against the unhardened plaster forming the first plaster mold surface 51. The unhardened plaster in the lower component LC over time is allowed to set and harden, holding the denture setup 10 or 10a, as the case may be, at the surface S1. In both cases, the interface surface portion ISP lies within the same plane as the surface S1.

Forming on the Hardened First Surface a Wax Gasket

Figure 3C:
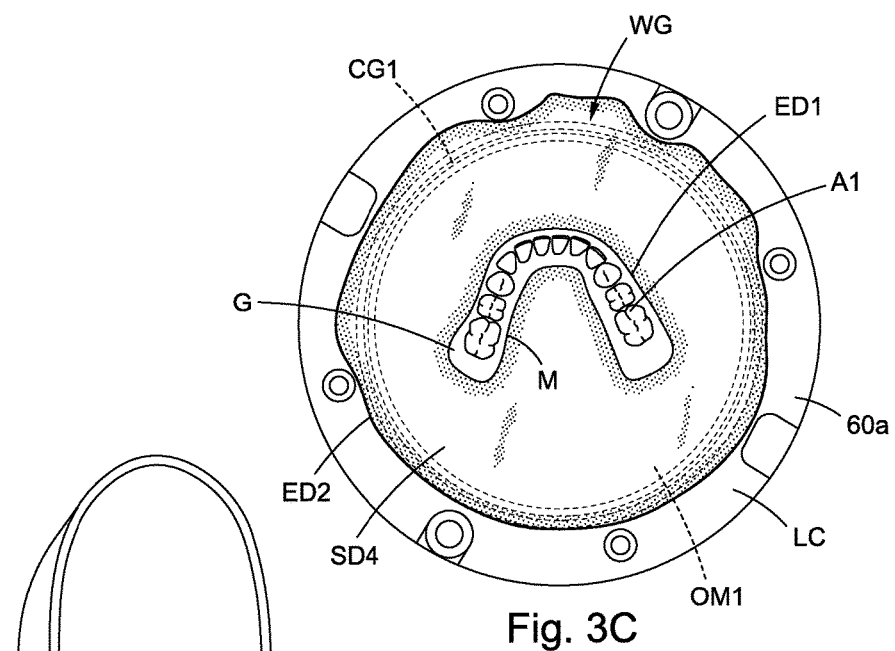
FIG. 3C is a plan view showing a wax gasket formed on the hardened exposed plaster surface of one part of the mold being made in the lower component of the two-component container.

As shown in FIG. 3C, a wax gasket WG that is generally flat with a thickness of about 1-2 millimeters is formed on top of the hardened, first plaster mold surface S1. As is conventional, flat strips of wax are applied to the surface S1 (FIG. 3B), and overlapping edges of the wax strips are bonded by melting to form the wax gasket WG. A first side SD3 (FIG. 5) of the wax gasket WG covers the surface S1 and surrounds the wax material forming the gum G. The wax gasket WG has an outer edge ED2 forming a perimeter that extends beyond the perimeter of the open mouth OM1 of the lower component LC and an inner edge ED1 that abuts the wax material of the gum G to form a margin M along this wax material corresponding to a gum line. The outer edge ED2 overlaps the circular groove CG1 in the lower component LC.

Assembling the First and Second Components with the Wax Gasket Between them

Figure 4:
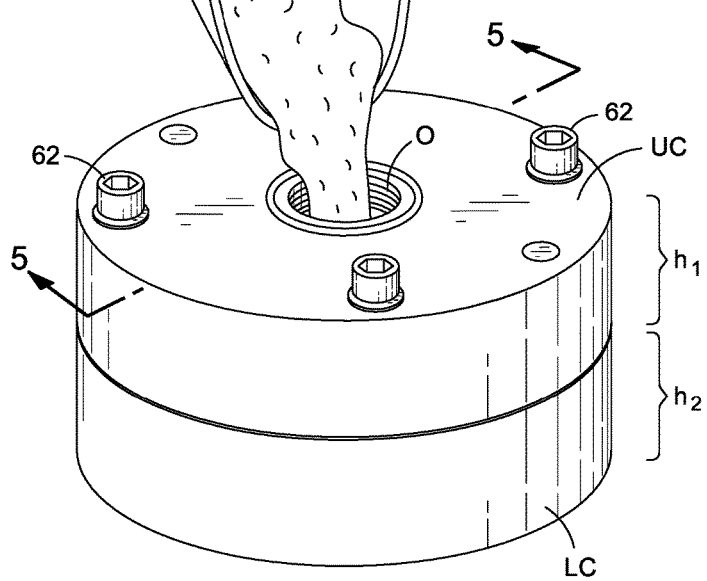
FIG. 4 is a perspective view of unhardened plaster being pored through the central opening in the upper component of the assembled two-component container, with the wax gasket between adjacent surfaces of the assembled two components of the two-part plaster mold for the denture setup as depicted in FIG. 5.
Figure 5:
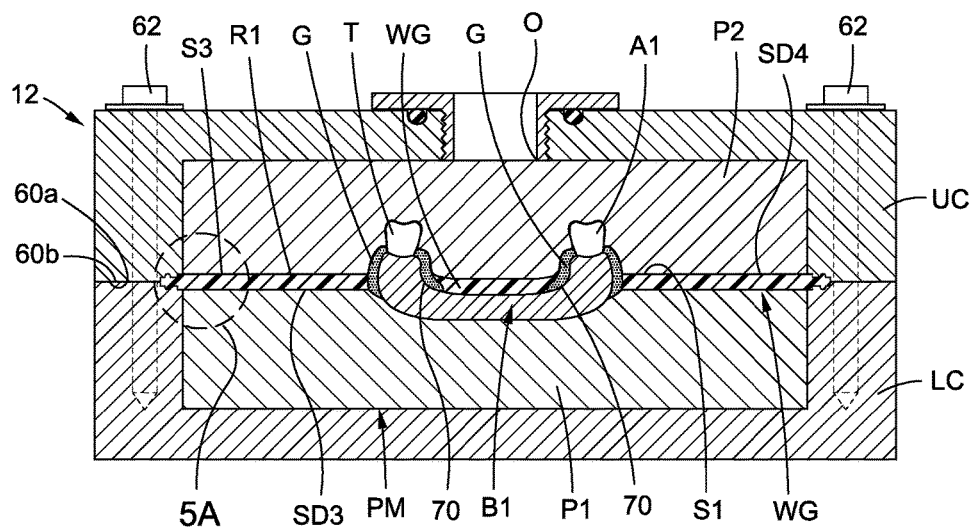
FIG. 5 is a cross-sectional view taken along line 5-5 of FIG. 4.
Figure 5A:
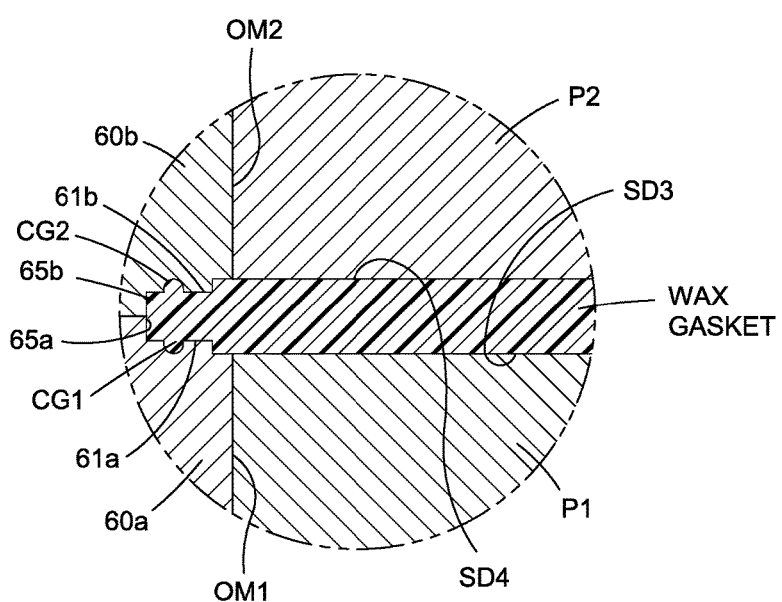
FIG. 5A is an enlarged fragmentary view taken along line 5A of FIG. 5.

As shown in FIGS. 1A and 4, the unfilled upper component UC of the container 12 and the filled lower component LC are assembled. As shown in FIG. 4, unhardened plaster is poured through a central threaded opening O in the upper component UC, covering the side SD4 (FIG. 5) of the wax gasket WG and filling the upper component UC with the unhardened plaster. Subsequently, the unhardened plaster is allowed to harden to form the part P2 of the two-part plaster mold PM. This part P2 includes a second plaster mold surface S3 (FIG. 6B) that is within the open mouth OM2 of the upper component UC upon filling the upper component UC with the unhardened plaster. With the assembly of the upper component UC and lower component LC, the wax gasket WG is between and abutting the first and second plaster mold surfaces S1 and S3, being firmly pressed against these surfaces, with the container flanges 60a and 60b engaging as depicted in FIGS. 5 and 5A. This forces the wax material along the outer perimeter of the wax gasket WG into the circular grooves CG1 and CG2, preventing plaster in the upper component UC from flowing into the lower component LC.

Figure 6:
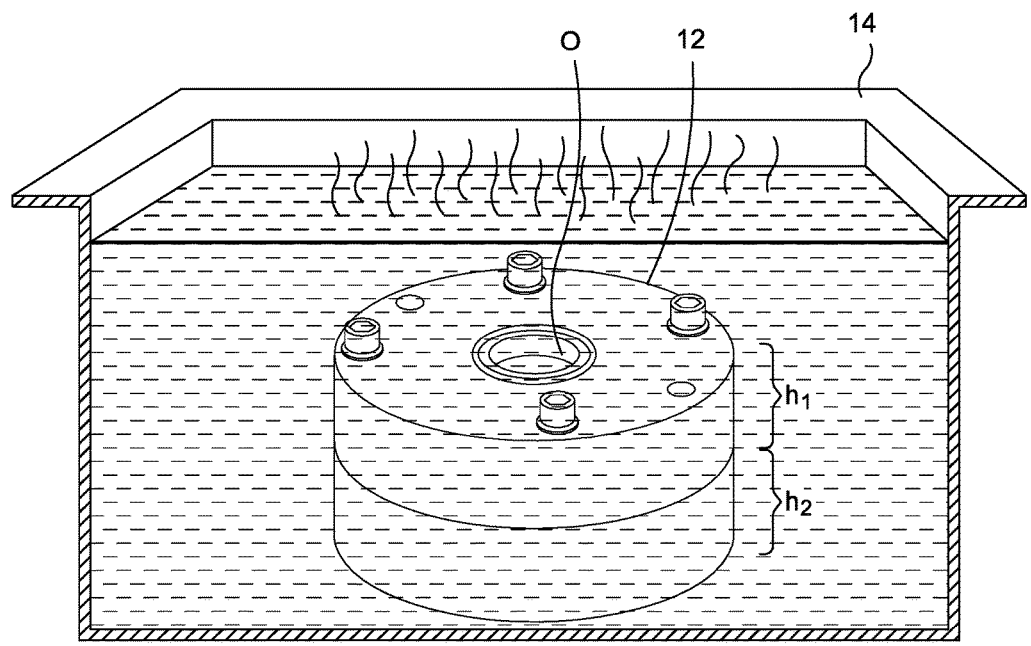
FIG. 6 is a perspective cross-sectional view of the assembled container in a hot water bath to melt the wax on the denture setup within the assembled container.
Figure 6A:
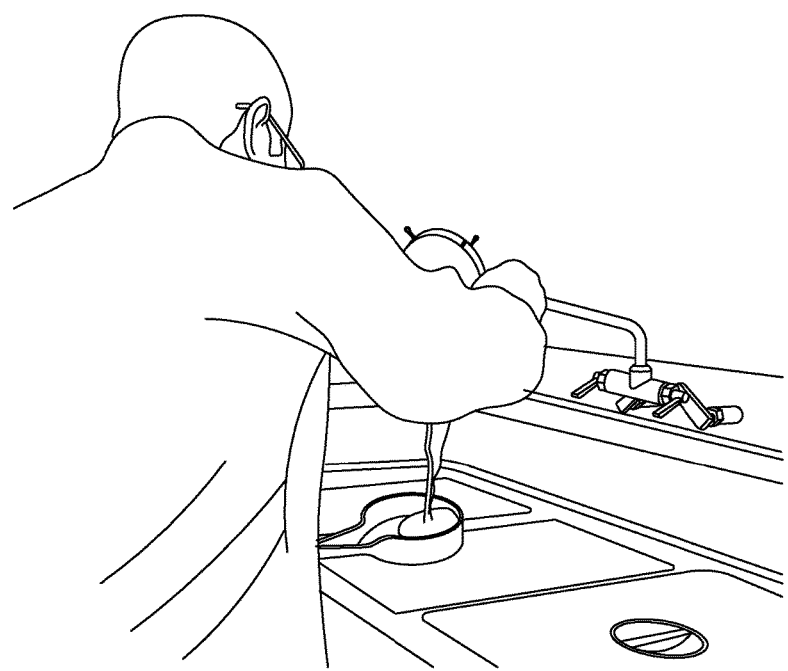
FIG. 6A is a perspective view of a technician, after disassembling the components of the container, manually washing an exposed hardened plaster surface of a mold part with hot water to remove wax from of this part.

Disassembling the Components of the Container and Removing the Wax Gasket and Wax Material Forming the Gum As illustrated in FIG. 6, the assembled container 12 is immersed in hot water in a tub 14. As the container 12 heats up, the wax gasket WG and the wax forming the naturally appearing gum G corresponding to the patient's gum melts away. Upon the wax gasket WG and wax gum G melting, the assembled container 12 is removed from the tub 14 of hot water and disassembled. The first plaster mold surface S1 and second plaster mold surface S3 of the two-part plaster mold PM are washed with hot water and thoroughly cleaned by a technician as shown in FIG. 6A.

Figures 6B, 6C:
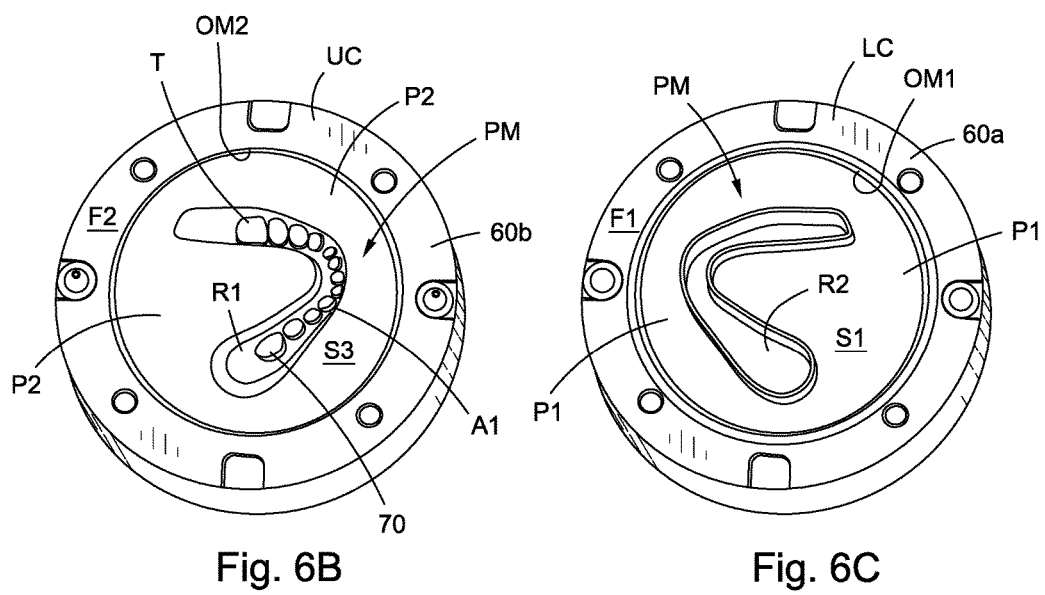
FIG. 6B is perspective view of the wax-free plaster surface filling the mouth of the one part of the two-part mold in the upper component of the disassembled container, showing base end of artificial teeth projecting outward from a curved indentation in the exposed surface of the upper part of the two-part plaster mold.
FIG. 6C is perspective view of the wax-free surface filling the mouth of the lower component of the disassembled container, showing a curved indentation in the exposed surface of the lower part of the two-part plaster mold.

Subsequently, as shown in FIGS. 6B and 6C, the components of the container 12 are disassembled to expose the hardened surfaces S1 and S3 of the parts P1 and P2, respectively, of the two-part plaster mold PM. As depicted in FIG. 6B, the surface S3 has a recess R1 with the array A1 of artificial teeth T positioned therein. As depicted in FIG. 6C, the surface S1 has a recess R2 complementary to the recess R1. The exposed roots 70 of the teeth T are shown in FIG. 6B, and the top edges 72 (FIG. 9B) of the teeth extend into the recess R1, projecting into the upper component UC and lodged in the recess R1.

Figures 7, 7A:
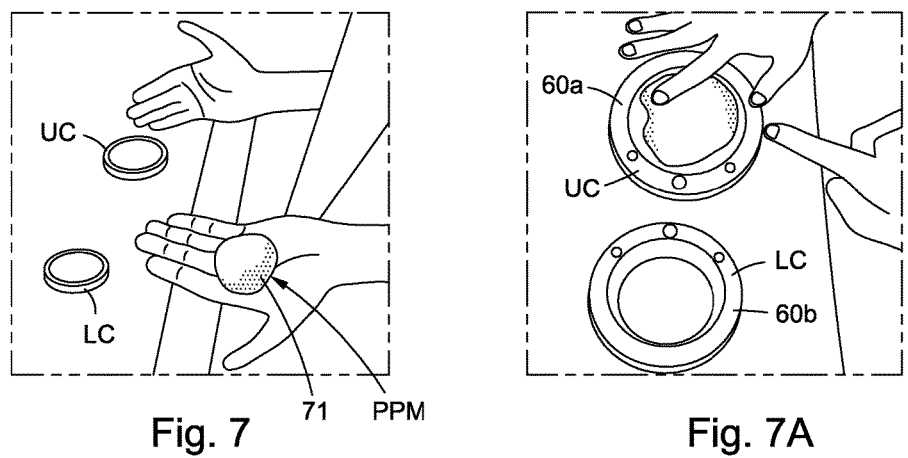
FIG. 7 is a schematic view of a technician rolling a polymerizable plastic material into a pliant ball.
FIG. 7A is a schematic view of the technician spreading the ball over the exposed surface of one part of the two-part mold to form upon reassembling of the components a membrane between the juxtaposed plaster surfaces of the parts of the two-part mold.

Applying to a Surface a Layer of Polymerizable Plastic Material and Reassembling the Container Components As illustrated in FIGS. 7, 7A, and 7B to at least one of the exposed plaster mold surfaces, for example the surface S3 of the upper component UC, a layer L of polymerizable plastic material PPM, for example, poly methyl methacrylate sold by Keer under the designation Lucitone 199, is applied, covering the recess R1 and the teeth T lodged therein. The technician first rolls the polymerizable plastic material PPM, which has a puttylike consistency, into a ball 71. As shown in FIGS. 7A and 7B, the technician spreads the ball 71 of plastic material PPM over the surface S3 to form a thin membrane M that covers the recess R1 of the artificial teeth T therein, filling the recess with the plastic material. The technician makes sure that the membrane M has a thickness of about 1-2 millimeters, and is devoid of any pinholes that would allow water to pass through the membrane, and an outer edge ED3 that extends beyond the perimeter of the open mouth OM2 of the upper component UC.

The technician again assembles the upper component UC and lower component LC with the recesses R1 and R2 in registration, compressing the membrane of polymerizable plastic material PPM between the first surface S1 and second surface S3. The assembled upper component UC and lower component LC form the container 12, which is then placed in a manually operated press 16 as shown in FIGS. 8A and 8B. Turning a handle 16a of the press 16 pushes the upper component UC towards and lower component LC to squeeze excess polymerizable plastic material out from between the surfaces S1 and S3 to form the teeth array A and polymerizable plastic material PPM into the structure depicted in FIG. 9B. It is at this point that the four bolts 62 are reinserted into the container 12 and tightened. The container 12 is then removed from the press 16 and completed for the next step of initiating polymerization.

Initiating Polymerization of the Polymerizable Plastic Material

Figure 9A:
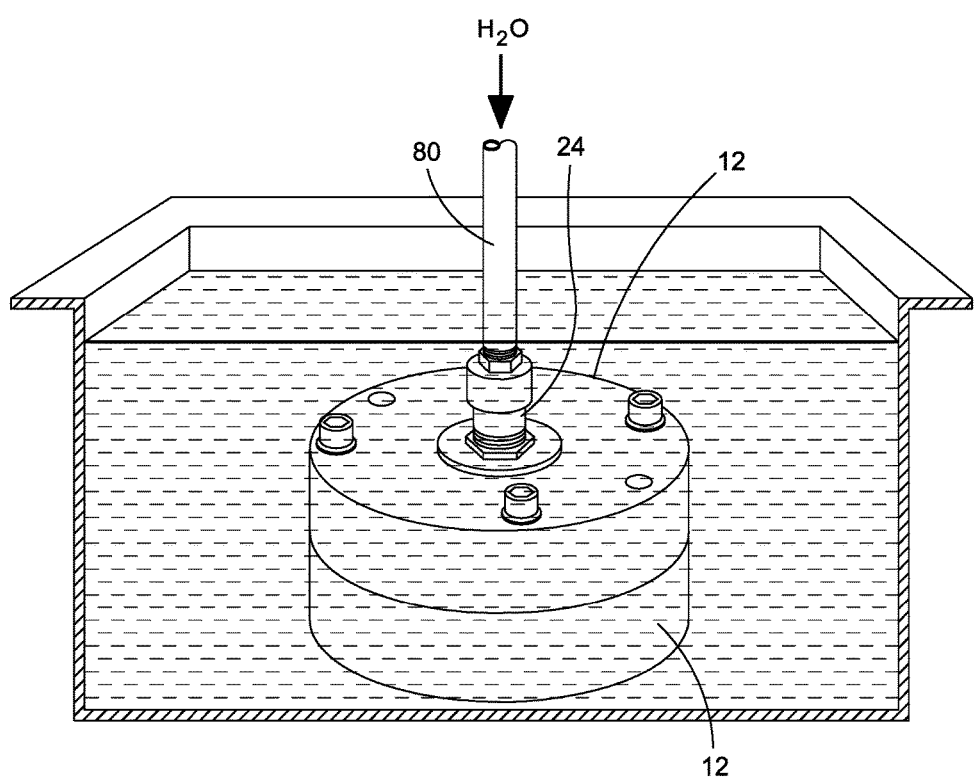
FIG. 9A is perspective view of the assembled container removed from the press shown in FIG. 8B and placed in a hot water bath and connected to a source of pressurized water.
Figure 9B:
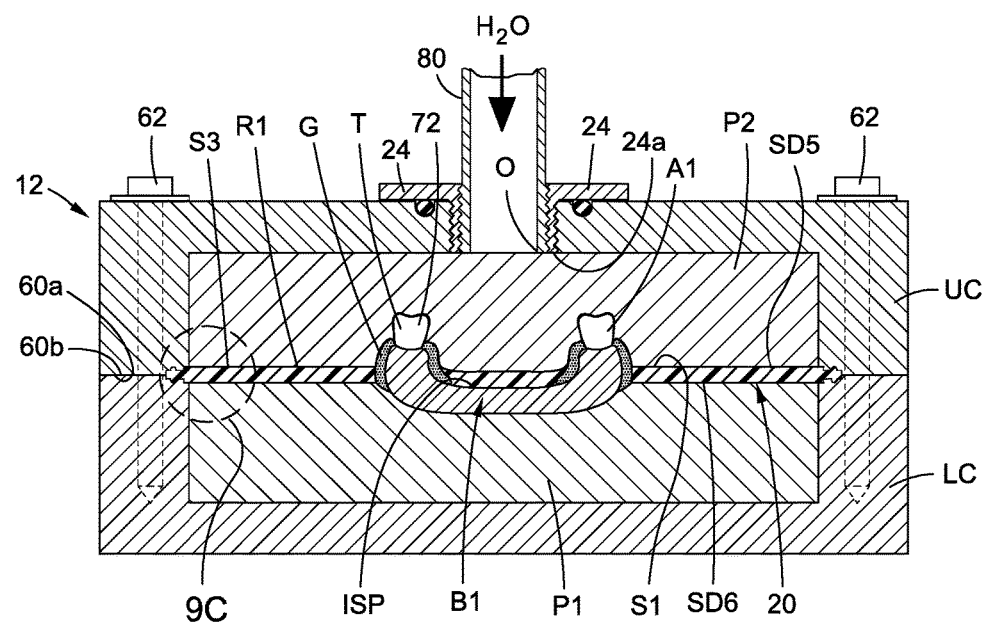
FIG. 9B is a cross-sectional view of the assembled container in the hot water bath illustrating the flow of water into upper mold and through the hardened porous plaster to apply the pressurized water against only the outer side of the of polymerized membrane material.

As depicted in FIG. 9A, the assembled container 12 is placed in a cold water tub and pressurized water is introduced into the upper component UC through a threaded pipe 80 connected to the inlet 24a (FIG. 1B) in the cap 24. To initiate polymerization the water in the tub is gradually heated to about 212 degrees Fahrenheit. As shown in FIG. 9B, the assembled container 12 now has a layer 20 of polymerizable plastic material overlying the teeth T lodged in the recess R1. The threaded cap 24 (FIG. 1B) is screwed into the threaded opening O, and the pipe 80 is screwed into the cap. The inlet 24a enables pressurized water to be introduced into the assembled container 12 at a high pressure above atmospheric pressure, for example in excess of 300 psi.

The hardened plaster part P2 is porous and the pressurized water so introduced percolates through this porous part and presses against the non-critical side SD5 of the thin layer 20 of polymerizable plastic material PPM so that this layer's opposite side SD6 bears against the plaster mold surface S1 (FIG. 7B) and the interface surface portion ISP. Polymerization of the plastic material PPM is initiated in a water bath at room temperature and gradually brought to a boil over the course of approximately 45 minutes. It is allowed to boil for an additional 120 minutes before terminating polymerization. Introducing into the assembled container 12 water at a high pressure above atmospheric pressure pushes the polymerizable plastic material PPM into the recess R1 to fill this recess with this plastic material and force the material away from the second mold surface S3 and against the critical interface surface portion ISP (FIG. 2) of the base B1 or B2, as the case may be. This forms from the polymerized plastic material a gum corresponding to the patient's gum that has an inside bearing or contact surface CS1 that has a topography complementary to the interior surface of the patient's mouth tissue bearing against this contact surface. Consequently, as shown best in FIG. 10B, the contact surface CS1 of the denture 11a so formed is complementary to the topographical features of the inside of the patient's mouth that contacts the denture. Thus, a contact surface on the denture is formed from the polymerized plastic material that mates closely with the interior surface tissue of the patient's mouth.

Removing any Excess Polymerized Plastic Material Formed Around the Artificial Teeth The container 12 is again disassembled and, the plaster parts P1 and P2, including the base B1 or B2, as the case may be, are broken, and the broken pieces are separated from the rigid unfinished polymer denture structure 30 shown in FIGS. 10A-10C. The unfinished denture structure 30 has a sheet 81 of the polymerized material extending outward therefrom that terminates in a marginal portion MP of polymerized plastic material formed around the artificial teeth T and polymerized plastic material forming a gum G2 corresponding to the patient's gum, i.e., the denture 11a or 11b, as the case may be.

Figure 9C:
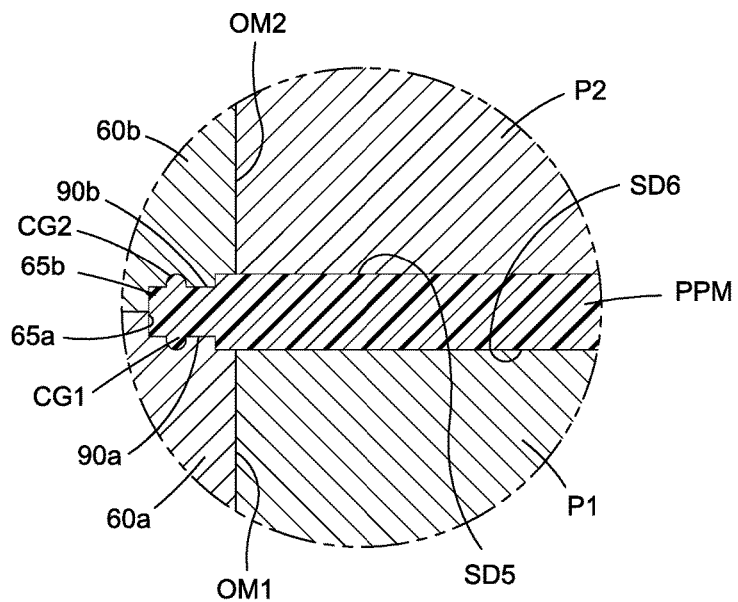
FIG. 9C is an enlarged fragmentary view taken along line 9C of FIG. 9B.

As best shown in FIG. 9C, the polymerizable plastic material PPM filled the aligned circular grooves CG1 and CG2 during formation of the unfinished denture structure 30 to produce a pair of aligned circular beads 90a and 90b along the outer perimeter the marginal portion MP. These beads 90a and 90b prevent excess shrinkage during polymerization.

The excess marginal portion MP is removed by trimming and grinding as depicted in FIG. 11A and polished as depicted in FIG. 11B, thereby providing a customized denture for an individual patient with polymerized plastic material forming the gum G2 corresponding to the patient's gum, thereby providing the customized denture for the individual patient.

Upper Full Denture

FIGS. 13A and 13B depict our finished upper full denture 11b, which is manufactured in the same manner as denture 11a as discussed above. FIG. 13A shows the exterior side SD5 of the denture 11b, and FIG. 13B shows the interior of the denture with the contact surface CS3.

SCOPE OF THE INVENTION

The above presents a description of the best mode we contemplate of carrying out our denture and method of manufacturing, and of the manner and process of making and using them, in such full, clear, concise, and exact terms as to enable a person skilled in the art to make and use. Our denture and method of manufacturing is, however, susceptible to modifications and alternate constructions from the illustrative embodiment discussed above which are fully equivalent. Consequently, it is not the intention to limit our denture and method of manufacturing to the particular embodiment disclosed. On the contrary, our intention is to cover all modifications and alternate constructions coming within the spirit and scope of our denture and method of manufacturing as generally expressed by the following claims, which particularly point out and distinctly claim the subject matter of our invention:

The invention claimed is:

1. A method of manufacturing a customized denture for an individual patient from a material that shrinks during the manufacturing to form a bearing surface of the manufactured denture that has a topography complementary to an interior surface of the patient's mouth that contacts the manufactured denture, said method including the steps of (a) preparing a denture setup that is a model of the denture being manufactured, said denture setup comprising a base having
  an interface surface portion having a topography that corresponds to the interior surface of the patient's mouth that bears against the manufactured denture,
  an external surface portion opposite the internal interface surface portion,
  an array of artificial teeth corresponding to the patient's teeth positioned upright on the interface surface portion and extending outward from the said interface surface portion to correctly match opposed patient teeth during biting, and
  a wax applied to the array of teeth and formed into a naturally appearing gum corresponding to the patient's gum, (b) providing a two-component container having a first component and a second component, said components configured to be assembled into a unitary container structure and having open mouths with matching shaped perimeters and facing each other in registration upon assembly, said components having complementary shaped perimeters of the mouths of the components that engage upon assembling said components to provide a seal, said assembled components adapted to receive water under pressure that is applied to the denture setup positioned within the assembled container, (c) with said components disassembled, filling the first component with an unhardened plaster to form a first part of a two-part plaster mold for retaining the denture setup, said first part including a first surface that is within the open mouth of the first component, (d) positioning the denture setup on the unhardened first surface at the mouth of the first component so the first surface and the interface surface portion lie in the same plane, and allowing the plaster in said first component to set and harden, (e) forming on said hardened first surface a wax gasket that has a first side that covers said first surface and the base of the denture set up to surround the wax material forming said naturally appearing gum corresponding to the patient's gum, said wax gasket having a perimeter that extends beyond the perimeter of the open mouth of the first component and an inner edge abuts the wax material to form a margin along the wax material corresponding to a patient's gum line, (f) assembling the first and second components with the wax gasket between said components, filling the second component with an unhardened plaster, and allowing the plaster in the second component to set and harden to form a second part of the two-part plaster mold for the denture setup, said second part including a second surface that is within the open mouth of the second component upon filling the upper component with the unhardened plaster, said second surface contacting a second side of the wax gasket upon assembly of the components, (g) disassembling the components of the container and removing the wax gasket and wax material forming said naturally appearing gum corresponding to the patient's gum to expose the hardened first and second surfaces of the parts of the two-part plaster mold, the second surface having a recess with the array of artificial teeth corresponding to the patient's teeth positioned therein and the first surface having a recess complementary to the recess with the teeth, (h) applying to the second surface a layer of polymerizable plastic material to form a membrane that covers the recess with the artificial teeth therein and has a perimeter that extends beyond the perimeter of the open mouths of the first and second components, (i) again assembling the first and second components and compressing the membrane of polymerizable plastic material between the first and second surfaces in the assembled components of the container, (j) initiating polymerization of the plastic material, and during polymerization, introducing into the assembled container water at a high pressure above atmospheric pressure to push the plastic material into the recesses to fill them with plastic material and force the plastic material away from the second mold surface and against the first mold surface to form from the polymerized plastic material a gum corresponding to the patient's gum and a bearing surface of the denture that has a topography complementary to the interior surface of the patient's mouth bearing against said bearing surface, and (k) removing any excess polymerized plastic material formed around the artificial teeth and polymerized plastic material forming a gum corresponding to the patient's gum, thereby providing the customized denture for the individual patient.

2. The method of claim 1 where the membrane has a thickness from 1 to 2 millimeters.

3. In a method of manufacturing a customized denture for an individual patient from a polymerizable polymeric material that shrinks during the manufacturing to form a bearing surface of the manufactured denture that has a topography complementary to an interior surface of the patient's mouth that contacts the manufactured denture, the improvement comprising applying the polymerizable polymeric material in the form of a membrane to an interface surface of a model of the customized denture that has a topography complementary to the interior surface of the patient's mouth that contacts the manufactured denture, said membrane having one side in contact with and covering the interface surface and a perimeter held in a stationary position during polymerization of the polymeric material, and subjecting another opposed side of the membrane to water at a pressure above atmospheric pressure to press the one side of the membrane against said interface surface to form from the polymerized polymeric material on said one side a bearing surface of the denture that mates closely with said interior surface of the patient's mouth.

* * * * *